(12) United States Patent
Cully et al.

(10) Patent No.: US 11,259,910 B2
(45) Date of Patent: Mar. 1, 2022

(54) TAPERED IMPLANTABLE DEVICE AND METHODS FOR MAKING SUCH DEVICES

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Marc A. Schlaud, Flagstaff, AZ (US); Arthur R. Studley, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 334 days.

(21) Appl. No.: 15/786,670

(22) Filed: Oct. 18, 2017

(65) Prior Publication Data
US 2018/0092733 A1 Apr. 5, 2018

Related U.S. Application Data

(63) Continuation of application No. 14/557,927, filed on Dec. 2, 2014, now Pat. No. 9,814,560.
(Continued)

(51) Int. Cl.
| | |
|---|---|
| *A61F 2/04* | (2013.01) |
| *B29C 55/00* | (2006.01) |
| *A61F 2/06* | (2013.01) |
| *B29C 55/24* | (2006.01) |
| *B29C 57/04* | (2006.01) |
| *B29C 55/22* | (2006.01) |

(Continued)

(52) U.S. Cl.
CPC .................. *A61F 2/04* (2013.01); *A61F 2/06* (2013.01); *A61F 2/95* (2013.01); *B29C 53/083* (2013.01); *B29C 53/086* (2013.01); *B29C 55/005* (2013.01); *B29C 55/22* (2013.01); *B29C 55/24* (2013.01); *B29C 55/30* (2013.01); *B29C 57/04* (2013.01); *A61F 2/07* (2013.01); *A61F 2240/00* (2013.01); *A61F 2240/001* (2013.01); *A61F 2250/0039* (2013.01); *A61F 2250/0058* (2013.01); *B29K 2027/18* (2013.01); *B29L 2031/7534* (2013.01)

(58) Field of Classification Search
CPC ...... A61F 2/04; A61F 2/06; A61F 2250/0039; A61F 2250/0018; A61F 2250/0028; A61F 2250/0029; B29K 2027/18
See application file for complete search history.

(56) References Cited

U.S. PATENT DOCUMENTS

| | | |
|---|---|---|
| 512,151 A | 1/1894 | Briggs |
| 3,425,418 A | 2/1969 | Chvapil et al. |

(Continued)

FOREIGN PATENT DOCUMENTS

| | | |
|---|---|---|
| CN | 1466165 A | 1/2004 |
| EP | 0117072 | 8/1984 |

(Continued)

OTHER PUBLICATIONS

European Search Report from EP18208417.8, dated Apr. 24, 2019, 8 pages.
(Continued)

*Primary Examiner* — Brian E Pellegrino (57) ABSTRACT

A tapered implantable device includes an ePTFE tubular member having a tapered length portion. The tapered length portion provides rapid recovery properties. The tapered length portion can feature a microstructure that includes a multiplicity of bent fibrils.

19 Claims, 3 Drawing Sheets

Related U.S. Application Data (60) Provisional application No. 61/912,339, filed on Dec. 5, 2013.

(51) Int. Cl.
  B29C 55/30 (2006.01)
  A61F 2/95 (2013.01)
  B29C 53/08 (2006.01)
  A61F 2/07 (2013.01)
  B29K 27/18 (2006.01)
  B29L 31/00 (2006.01)

(56) References Cited

U.S. PATENT DOCUMENTS

| | | |
|---|---|---|
| 3,814,137 A | 6/1974 | Martinez |
| 3,914,802 A | 10/1975 | Reick |
| 3,953,566 A | 4/1976 | Gore |
| 4,133,927 A | 1/1979 | Tomodoa et al. |
| 4,177,334 A | 12/1979 | Okita |
| 4,187,390 A | 2/1980 | Gore |
| 4,193,138 A | 3/1980 | Okita |
| 4,208,745 A | 6/1980 | Okita |
| 4,229,838 A | 10/1980 | Sumitomo |
| 4,279,245 A | 7/1981 | Takagi et al. |
| 4,283,448 A | 8/1981 | Bowman |
| 4,304,010 A | 12/1981 | Mano |
| 4,321,711 A | 3/1982 | Mano |
| 4,347,204 A | 8/1982 | Takagi et al. |
| 4,416,028 A | 11/1983 | Eriksson et al. |
| 4,443,511 A | 4/1984 | Worden et al. |
| RE31,618 E | 7/1984 | Mano |
| 4,474,630 A | 10/1984 | Planck et al. |
| 4,478,898 A | 10/1984 | Kato |
| 4,550,447 A | 11/1985 | Seiler, Jr. et al. |
| 4,604,762 A | 8/1986 | Robinson |
| 4,613,544 A | 9/1986 | Burleigh |
| 4,619,641 A | 10/1986 | Schanzer |
| 4,657,544 A | 4/1987 | Pinchuk |
| 4,687,482 A | 8/1987 | Hanson |
| 4,692,369 A | 9/1987 | Nomi |
| 4,731,073 A | 3/1988 | Robinson |
| 4,739,013 A | 4/1988 | Pinchuk |
| 4,743,252 A | 5/1988 | Martin, Jr. et al. |
| 4,743,480 A | 5/1988 | Campbell et al. |
| 4,759,757 A | 7/1988 | Pinchuk |
| 4,787,921 A | 11/1988 | Shibata et al. |
| 4,804,381 A | 2/1989 | Turina et al. |
| 4,810,749 A | 3/1989 | Pinchuk |
| 4,816,339 A | 3/1989 | Tu et al. |
| 4,850,999 A | 7/1989 | Planck |
| 4,857,069 A | 8/1989 | Kira |
| 4,871,361 A | 10/1989 | Kira |
| 4,875,468 A | 10/1989 | Krauter et al. |
| 4,877,661 A | 10/1989 | House et al. |
| 4,882,113 A | 11/1989 | Tu |
| 4,891,407 A | 1/1990 | Mitchell |
| 4,921,495 A | 5/1990 | Kira |
| 4,932,964 A | 6/1990 | Bittmann et al. |
| 4,945,125 A | 7/1990 | Dillon et al. |
| 4,955,899 A | 9/1990 | Coma et al. |
| 4,957,669 A | 9/1990 | Primm |
| 4,969,896 A | 11/1990 | Shors |
| 4,973,609 A | 11/1990 | Browne |
| 5,024,671 A | 6/1991 | Tu |
| 5,026,513 A | 6/1991 | House |
| 5,061,276 A | 10/1991 | Tu |
| 5,064,593 A | 11/1991 | Tamaru et al. |
| 5,066,683 A | 11/1991 | Dillon et al. |
| 5,071,609 A | 12/1991 | Tu et al. |
| 5,084,065 A | 1/1992 | Weldon et al. |
| 5,100,422 A | 3/1992 | Berguer et al. |
| 5,104,400 A | 4/1992 | Berguer et al. |
| 5,116,360 A | 5/1992 | Pinchuk et al. |
| 5,123,917 A | 6/1992 | Lee |
| 5,128,092 A | 7/1992 | Asaumi et al. |
| 5,133,742 A | 7/1992 | Pinchuk |
| 5,152,782 A | 10/1992 | Kowligi et al. |
| 5,192,310 A | 3/1993 | Herweck et al. |
| 5,217,797 A | 6/1993 | Knox et al. |
| 5,229,431 A | 7/1993 | Pinchuk |
| 5,290,271 A | 3/1994 | Jernberg |
| 5,320,888 A | 6/1994 | Stevens |
| 5,354,329 A | 10/1994 | Whalen |
| 5,358,516 A | 10/1994 | Myers et al. |
| 5,370,681 A | 12/1994 | Herweck et al. |
| 5,453,235 A | 9/1995 | Calcote et al. |
| 5,466,252 A | 11/1995 | Soukup et al. |
| 5,476,589 A | 12/1995 | Bacino |
| 5,584,876 A | 5/1996 | Bruchman et al. |
| 5,527,353 A | 6/1996 | Schmitt |
| 5,529,820 A | 6/1996 | Nomi et al. |
| 5,549,664 A | 8/1996 | Hirata et al. |
| 5,556,426 A | 9/1996 | Popadiuk et al. |
| 5,607,478 A | 3/1997 | Lentz et al. |
| 5,609,624 A | 3/1997 | Kalis |
| 5,620,763 A | 4/1997 | House et al. |
| 5,628,782 A | 5/1997 | Myers et al. |
| 5,628,788 A | 5/1997 | Pinchuk |
| 5,641,373 A | 6/1997 | Shannon et al. |
| 5,647,400 A | 7/1997 | Jani et al. |
| 5,665,114 A | 9/1997 | Weadock et al. |
| 5,700,287 A | 12/1997 | Myers et al. |
| 5,708,044 A | 1/1998 | Branca |
| 5,716,395 A | 2/1998 | Myers et al. |
| 5,716,660 A | 2/1998 | Weadock et al. |
| 5,718,973 A | 2/1998 | Lewis et al. |
| 5,735,892 A | 4/1998 | Myers et al. |
| 5,749,880 A | 5/1998 | Banas et al. |
| 5,788,626 A | 8/1998 | Thompson |
| 5,789,047 A | 8/1998 | Sasaki et al. |
| 5,800,510 A | 9/1998 | Schmitt |
| 5,800,512 A | 9/1998 | Lentz et al. |
| 5,800,514 A | 9/1998 | Nunez |
| 5,824,050 A | 10/1998 | Karwoski et al. |
| 5,840,240 A | 11/1998 | Stenoien |
| 5,843,173 A | 12/1998 | Shannon et al. |
| 5,851,229 A | 12/1998 | Lentz et al. |
| 5,851,230 A | 12/1998 | Lentz et al. |
| 5,866,217 A | 2/1999 | Stenoien et al. |
| 5,897,587 A | 4/1999 | Martakos et al. |
| 5,904,967 A | 5/1999 | Ezaki et al. |
| 5,910,168 A | 6/1999 | Myers et al. |
| 5,931,865 A | 8/1999 | Silverman et al. |
| 5,976,192 A | 11/1999 | McIntyre et al. |
| 6,001,125 A | 12/1999 | Golds et al. |
| 6,016,848 A | 1/2000 | Egres et al. |
| 6,027,779 A | 2/2000 | Campbell et al. |
| 6,036,724 A | 3/2000 | Lentz et al. |
| 6,039,755 A | 3/2000 | Edwin |
| 6,042,666 A | 3/2000 | Karwoski et al. |
| 6,053,939 A | 4/2000 | Okuda et al. |
| 6,056,970 A | 5/2000 | Greenawalt et al. |
| 6,080,198 A | 6/2000 | Lentz et al. |
| 6,099,557 A | 8/2000 | Schmitt |
| 6,159,565 A | 12/2000 | Campbell et al. |
| 6,165,211 A | 12/2000 | Thompson |
| 6,187,054 B1 | 2/2001 | Colone et al. |
| 6,203,735 B1 | 3/2001 | Edwin |
| 6,267,834 B1 | 7/2001 | Shannon et al. |
| 6,287,337 B1 | 9/2001 | Martakos et al. |
| 6,319,279 B1 | 11/2001 | Shannon et al. |
| 6,328,762 B1 | 12/2001 | Anderson et al. |
| 6,338,904 B1 | 1/2002 | Patnaik et al. |
| 6,346,273 B1 | 2/2002 | Saettone |
| 6,368,347 B1 | 4/2002 | Maini et al. |
| 6,416,537 B1 | 7/2002 | Martakos et al. |
| 6,428,571 B1 | 8/2002 | Lentz et al. |
| 6,436,135 B1 | 8/2002 | Goldfarb |
| 6,517,571 B1 | 2/2003 | Brauker et al. |
| 6,517,858 B1 | 2/2003 | LeMoel et al. |
| 6,521,284 B1 | 2/2003 | Parsons et al. |
| 6,534,084 B1 | 3/2003 | Vyakarnam et al. |
| 6,541,589 B1 | 4/2003 | Baillie |

(56) References Cited

U.S. PATENT DOCUMENTS

| | | |
|---|---|---|
| 6,547,820 B1 | 4/2003 | Staudenmeier |
| 6,589,468 B1 | 7/2003 | Schmitt |
| 6,663,614 B1 | 12/2003 | Carter |
| 6,712,919 B2 | 3/2004 | Ruefter et al. |
| 6,716,239 B2 | 4/2004 | Sowinski |
| 6,719,783 B2 | 4/2004 | Lentz et al. |
| 6,790,226 B2 | 9/2004 | Edwin et al. |
| 6,814,753 B2 | 11/2004 | Schmitt |
| 6,827,737 B2 | 12/2004 | Hill et al. |
| 6,863,686 B2 | 3/2005 | Shannon et al. |
| 6,926,735 B2 | 8/2005 | Henderson |
| 6,939,377 B2 | 9/2005 | Jayaraman et al. |
| 7,056,336 B2 | 6/2006 | Armstrong et al. |
| 7,056,387 B2 | 6/2006 | Van Der Steur |
| 7,108,701 B2 | 9/2006 | Evens et al. |
| 7,147,617 B2 | 12/2006 | Henderson et al. |
| 7,244,271 B2 | 7/2007 | Lentz et al. |
| 7,297,158 B2 | 11/2007 | Jensen |
| 7,306,729 B2 | 12/2007 | Bacino et al. |
| 7,351,257 B2 | 4/2008 | Kaldany |
| 7,396,363 B2 | 7/2008 | Frid |
| 7,452,374 B2 | 11/2008 | Hain et al. |
| 7,510,571 B2 | 3/2009 | Spiridigliozzi et al. |
| 7,531,611 B2 | 5/2009 | Sabol et al. |
| 7,553,326 B2 | 6/2009 | Sweet et al. |
| 7,560,006 B2 | 7/2009 | Rakos et al. |
| 8,029,563 B2 | 10/2011 | House |
| 8,637,144 B2 | 1/2014 | Ford |
| 8,906,087 B2 | 12/2014 | House |
| 9,139,669 B2 | 9/2015 | Xu et al. |
| 10,357,385 B2 | 7/2019 | Schlaud et al. |
| 2002/0058991 A1 | 5/2002 | Schmitt |
| 2002/0138129 A1 | 9/2002 | Armstrong |
| 2003/0004559 A1 | 1/2003 | Lentz et al. |
| 2003/0027775 A1 | 2/2003 | Wallace |
| 2003/0060871 A1 | 3/2003 | Hill et al. |
| 2003/0100859 A1 | 5/2003 | Henderson et al. |
| 2003/0139806 A1 | 7/2003 | Haverkost et al. |
| 2003/0153983 A1 | 8/2003 | Miller et al. |
| 2004/0024442 A1 | 2/2004 | Sowinski et al. |
| 2004/0033364 A1 | 2/2004 | Spiridigliozzi et al. |
| 2004/0049264 A1 | 3/2004 | Sowinksi et al. |
| 2004/0054406 A1 | 3/2004 | Dubson et al. |
| 2004/0122507 A1 | 6/2004 | Henderson |
| 2004/0182511 A1 | 9/2004 | Rakos et al. |
| 2004/0193242 A1 | 9/2004 | Lentz et al. |
| 2004/0215337 A1 | 10/2004 | Hain et al. |
| 2004/0265352 A1 | 12/2004 | Kaldany |
| 2005/0137677 A1 | 6/2005 | Rush |
| 2005/0187607 A1 | 8/2005 | Akhtar et al. |
| 2005/0240261 A1 | 10/2005 | Rakos |
| 2005/0249776 A1 | 11/2005 | Chen et al. |
| 2006/0041318 A1 | 2/2006 | Shannon |
| 2007/0116736 A1 | 5/2007 | Argentieri et al. |
| 2007/0276474 A1 | 11/2007 | Llanos et al. |
| 2007/0293808 A1 | 12/2007 | Williams et al. |
| 2008/0027534 A1 | 1/2008 | Edwin et al. |
| 2008/0097592 A1 | 4/2008 | Fitzpatrick |
| 2008/0195026 A1 | 8/2008 | Kim |
| 2008/0195079 A1 | 8/2008 | Moore et al. |
| 2009/0270973 A1 | 10/2009 | Chen et al. |
| 2011/0054586 A1 | 3/2011 | Mayberry |
| 2012/0130477 A1 | 5/2012 | Gessaroli |
| 2015/0157444 A1 | 6/2015 | Cully et al. |
| 2019/0343663 A1 | 11/2019 | Schlaud et al. |

FOREIGN PATENT DOCUMENTS

| | | |
|---|---|---|
| EP | 0256748 | 2/1988 |
| EP | 0266035 | 5/1988 |
| EP | 0391586 A2 | 10/1990 |
| EP | 656196 A1 | 7/1995 |
| EP | 1131113 B1 | 2/2000 |
| EP | 1101458 | 5/2001 |
| EP | 1925270 | 5/2008 |
| GB | 2033232 | 5/1980 |
| GB | 1590101 | 5/1981 |
| GB | 2222954 | 3/1990 |
| JP | 6343688 | 12/1994 |
| JP | 2739420 | 3/1995 |
| JP | 8238263 | 9/1996 |
| JP | 11099163 | 4/1999 |
| JP | 5176947 | 7/2010 |
| JP | 5474514 | 6/2011 |
| JP | 5925725 | 11/2014 |
| WO | WO-1995010247 | 4/1995 |
| WO | WO-1996007370 A1 | 3/1996 |
| WO | WO-9826731 | 6/1998 |
| WO | WO-2001021107 | 3/2001 |
| WO | WO-2001032382 | 5/2001 |
| WO | WO-2001067991 | 9/2001 |
| WO | WO-2002013675 A2 | 2/2002 |
| WO | WO-03015837 | 2/2003 |
| WO | WO-2003084440 | 10/2003 |
| WO | WO-2004060209 | 7/2004 |
| WO | WO-2004096307 | 11/2004 |
| WO | WO-2006/007214 | 1/2006 |
| WO | WO-2006026725 | 3/2006 |
| WO | WO-2006038031 | 4/2006 |
| WO | WO-2006058322 A2 | 6/2006 |
| WO | WO-2006085044 A1 | 8/2006 |
| WO | WO-2007061787 | 5/2007 |
| WO | WO-2007113494 | 10/2007 |
| WO | WO-2007127802 | 11/2007 |
| WO | WO-2007137211 | 11/2007 |

OTHER PUBLICATIONS

Berman M, Pearce W, et al, The use of Gore-Tex E-PTFE bonded to silicone rubber as an alloplastic implant material. Laryngoscope 1986; v96 n5: 480-483.

GORE® Acuseal Cardiovascular Patch Product Information, Jun. 2014, 40 pages.

International Search Report and Written Opinion for PCT/US2014/068411 dated Feb. 12, 2015, corresponding to U.S. Appl. No. 14/557,927, 9 pages.

International Search Report and Written Opinion for PCT/US2016/035857 dated Aug. 4, 2016, corresponding to U.S. Appl. No. 15/173,361, 11 pages.

LeMatire Expedial Vascular Access Graft Product Information/Instructions For Use.

Lumsden AB, Chen C et al. Nonporous silicone polymer coating of expanded polytetrafluoroethylene grafts reduces graft neointimal hyperplasia in dog and baboon models. Journal of Vascular Surgery 1996; v24 n5: 825-833.

Perma-Seal Dialysis Access Graft Instructions for use.

Perma-Seal Dialysis Access Graft Patient Education Brochure.

Sonoda H, Takamizawa K et al. Coaxial double-tubular compliant arterial graft prosthesis: time-dependent morphogenesis and compliance changes after implantation. J Biomed Mater Res 2003: 65A: 170-181.

Sonoda H, Takamizawa K et al. Small-diameter compliant arterial graft prosthesis: Design concept of coaxial double tubular graft and its fabrication. J Biomed Mater Res 2011; 55: 266-276.

International Preliminary Report on Patentability received for PCT Patent Application No. PCT/US2016/035857, dated Dec. 14, 2017, 8 pages.

FIG. 1

DIRECTION OF EXPANSION

DIRECTION OF COMPRESSION

TAPERED IMPLANTABLE DEVICE AND METHODS FOR MAKING SUCH DEVICES

CROSS-REFERENCE TO RELATED APPLICATION

This application is a continuation of U.S. patent application Ser. No. 14/557,927, filed Dec. 2, 2014, which claims the benefit of U.S. Provisional Application 61/912,339, filed Dec. 5, 2013, both of which are incorporated herein by reference in their entireties for all purposes.

TECHNICAL FIELD

This document relates to tapered implantable devices and methods for making such devices that may be used for providing a lumen for fluid flow in bodily cavities, organs, and vessels within a patient.

BACKGROUND

Medical devices are frequently used to treat the anatomy of patients. Such devices can be permanently or semi-permanently implanted in the anatomy to provide treatment to the patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and delivered to a treatment site.

Devices such as grafts and stent-grafts are used in a variety of places in the human body to repair, support, and/or replace anatomical lumens, such as blood vessels, respiratory ducts, gastrointestinal ducts, and the like. Such devices can, for example, provide lumens for fluid flow. In such configurations, flexible and durable devices are needed.

In various applications, such as particular vascular applications, it is desirable to utilize a graft or artificial lumen having a tapered length portion. Tapered length portion and/or grafts may also be useful in connecting discreet grafts or tubes of differing diameters. As such, there is an ongoing need to provide tapered implantable devices, such as grafts and/or stent-grafts, which have improved flexibility and/or rapid recovery properties. Such devices may improve characteristics of the blood flow of a patient and reduce thrombosis.

SUMMARY

In a first general aspect, a tapered implantable device for repairing or replacing a lumen in the body of a patient comprises a tubular member, such as an ePTFE tubular member, having a tapered portion. The tapered portion includes a multiplicity of substantially bent fibrils, providing a region having rapid recovery properties.

In various implementations, a tapered implantable device in accordance with the present disclosure is formed by stretching a smaller diameter polymeric tubular member over a first mandrel having larger and smaller opposing ends and an intermediate tapered length segment to create a first tapered length portion on the polymeric tubular mandrel. The tubular member is then longitudinally compressed on a second mandrel to form the tapered implantable device by converting the first tapered length portion into a second tapered length portion having a multiplicity of bent fibrils. The tapered implantable device is then removed from the second mandrel and prepared for implantation into the anatomy of a patient.

The details of one or more embodiments are set forth in the accompanying drawings and the description below. Other features, objects, and advantages will be apparent from the description and the drawings, and from the claims.

Like reference symbols in the various drawings indicate like elements. It should also be noted that the accompanying drawing figures referred to herein are not all drawn to scale, but may be exaggerated to illustrate various aspects of the present disclosure, and in that regard, the drawing figures should not be construed as limiting.

DETAILED DESCRIPTION OF THE ILLUSTRATED EMBODIMENTS

This document describes devices, systems, and methods that are useful, for example, for repairing, supporting, and/or replacing anatomical lumens. Several implantable medical devices are described herein, and in general any of the features described with respect to a particular device may also be used with any of the other devices described herein. In some examples, one or more features described with respect to a particular device may be added to or included with another device. Also, various combinations or sub-combinations of any of the features described herein may generally be used with any of the devices described herein.

In general, any of the implantable devices described herein can be delivered to, and deployed at, an in vivo deployment site within a body of a patient using various minimally invasive surgical techniques. Likewise, these devices may also be surgically implanted via vascular surgical techniques.

Further, any of the implantable medical devices described herein can be delivered to, and deployed at, an in vivo deployment site within a body of a patient using various minimally invasive transcatheter deployment techniques.

Any of the implantable medical devices discussed herein can be used to repair, replace, and/or provide support to a body lumen. In various embodiments, implantable medical devices of the present disclosure can be used in a body lumen, including those within the circulatory and gastrointestinal systems.

As used herein, "implantable" means implanted in the body of a patient for more than 29 days.

As used herein, "taper" or "tapered" generally refers to a region of transition from one portion of a device to another portion of the same device. Most typically, a taper transitions a portion of a tubular device having a circular transverse cross-section with a larger inside diameter to another portion of the same device having a circular transverse cross-section with a smaller inner diameter. The region can be symmetrically or asymmetrically conical, or may be shaped to include bumps, reversals, or flares.

For the sake of consistency and clarity, the term "portion" is used to identify a length of, for example, a tubular member. The term "segment" is used to identify a length of, for example, a first or second mandrel. These terms are not intended to be limiting, and are chosen primarily to assist in understanding the references to various tubular members and mandrels.

Figure 1:
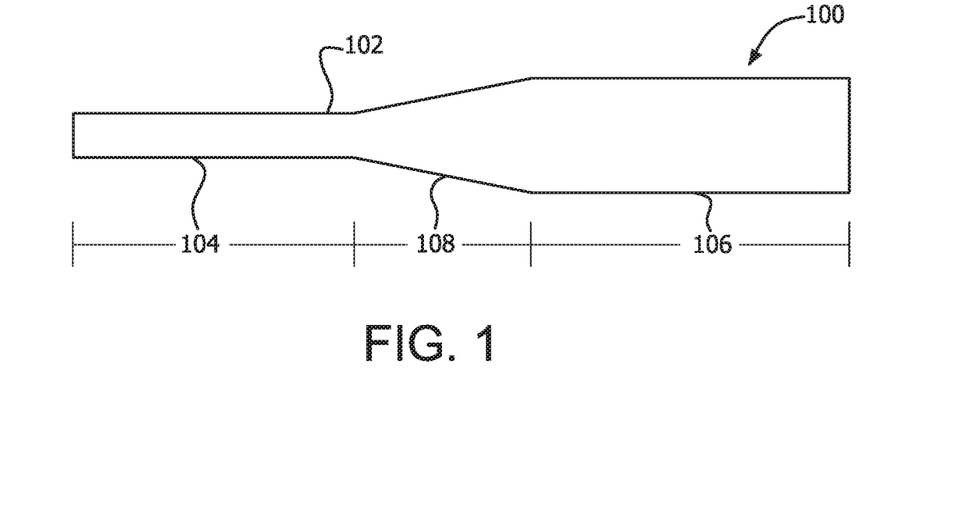
FIG. 1 is a side view of a portion of a tapered implantable device in accordance with the present disclosure.

FIG. 1 illustrates an example tapered implantable device 100 comprising a polymeric tubular member 102 having a first smaller diameter length portion 104, a second larger diameter length portion 106, and a tapered length portion 108. Polymeric tubular member 102 can, for example, comprise an axially compressible polymeric material, such as a longitudinally extruded and expanded polymer, including expanded polytetrafluoroethylene ("ePTFE"), expanded modified PTFE, expanded copolymers of PTFE, nylons, polycarbonates, polyethylenes, polypropylenes, polyurethanes and the like. In various embodiments, polymeric tubular member 102 comprises an extruded ePTFE tube, such as the tubes described in U.S. Pat. Nos. 3,953,566 and 4,187,390. In other embodiments, polymeric tubular member 102 comprises a wrapped ePTFE film tube. For example, member 102 can comprise a tube made from an ePTFE film that has been cigarette wrapped on the surface of a mandrel or, alternatively, has been helically wrapped on the surface of a mandrel. Such ePTFE films of this type can be made generally as taught by U.S. Pat. Nos. 3,953,566 and 4,187,390. In yet other embodiments, member 102 can comprise a polymeric open celled material. However, any suitable polymeric tubular member is within the scope of the present disclosure.

In various embodiments, polymeric tubular member 102 comprises an ePTFE tube having microstructure of nodes interconnected by fibrils. The microstructure of polymeric tubular member 102 can comprise a multiplicity of fibrils having a mean fibril length. Mean fibril length can be determined, for example, by examining a photomicrograph of the surface of polymeric tubular member 102 and by taking the mean of ten measurements made in the predominant direction of the fibrils between nodes connected by fibrils. First, a photomicrograph is made of a representative region of the sample surface, of adequate magnification to show at least five sequential fibrils within the length of the photomicrograph. A series of five measurements are taken along a straight line drawn onto the surface of the photomicrograph in the predominant direction of the fibrils followed by a second series of five measurements made along a second line drawn parallel to the first. A measurement constitutes the distance between adjacent nodes connected by at least one fibril. The ten measurements obtained by this method are averaged to obtain the mean fibril length of the region.

Figure 2:
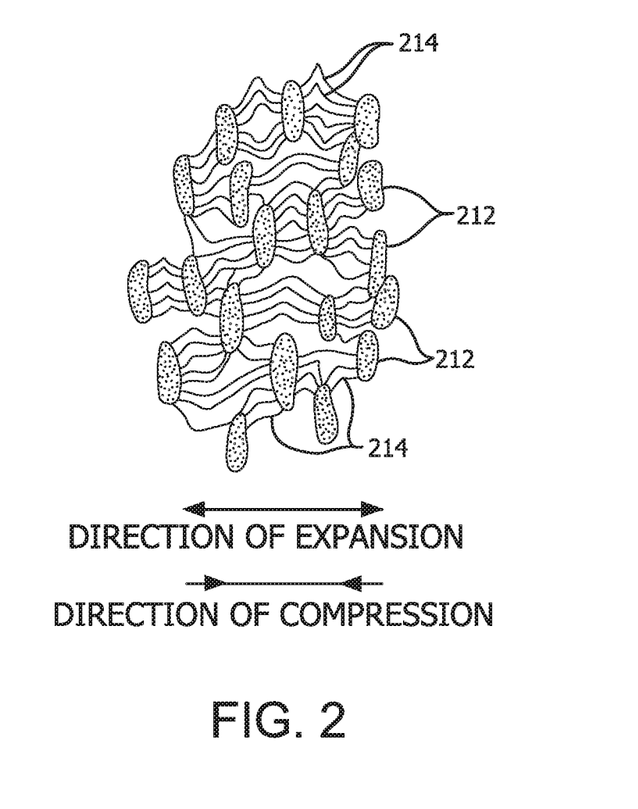
FIG. 2 is a schematic representation of a microstructure of ePTFE material in accordance with the present disclosure.

For example, as illustrated in FIG. 2, any or all of length portions 102, 108, and 106 can have a multiplicity of bent fibrils 214.

Tapered length portion 108 can, for example, possess a rapid recovery property, i.e., a spring-like property. Rapid recovery as herein defined is the difference between the extended length of a material and the recovered length with respect to the recovered length, as generally described in U.S. Pat. No. 5,026,513. The extended length is the length of material under tensile load and recovered length is the length of material. In various embodiments, rapid recovery can be quantified by the following equation:

$$RR\% = \frac{(l_t - l_r)}{(l_r)} \times 100\%$$

where $l_t$ is the length of the tapered length portion 108 when extended axially under 1% maximum tensile force, and $l_r$ is the length of the tapered portion five seconds after the release of the tensile force. Tapered length portion 108 having rapid recovery properties can, for example, exhibit improved bending characteristics and improved resistance to kinking, constriction, and/or collapse under bending.

In various embodiments, tapered length portion 108 can comprise a uniform frustoconical section. In such embodiments, tapered length portion 108 expands in the manner of a uniform frustoconical section from a diameter of first smaller diameter length portion 104 to a diameter of second larger diameter length portion 106.

In other embodiments, tapered length portion 108 comprises a non-uniform shape. For example, tapered length portion 108 can expand from a diameter of first smaller diameter length portion 104 to a diameter of second larger diameter length portion 106 in a non-uniform manner, such as a curved, non-linear shape. Any shape of tapered length portion 108 is within the scope of the present disclosure.

A method for making a tapered implantable device of the present disclosure is described as follows. A polymeric tubular member is fitted over a first mandrel having first, longer tapered length segment to form a first tapered length portion along a portion of the length of the polymeric tubular member. The polymeric tubular member is removed from the first mandrel and fitted over and axially compressed onto a second mandrel having a second, shorter tapered length segment to form the first tapered length portion into a second tapered length portion. A female die can optionally be used assist in compression of the polymeric tubular member on the second mandrel, particularly over the second tapered length portion. The polymeric tubular member can then be removed from the second mandrel.

Figure 3A:
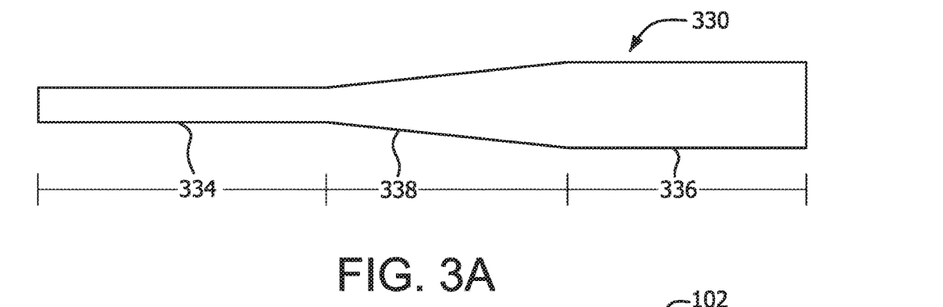
FIG. 3A is a side view of a first tapered mandrel.
Figure 3B:
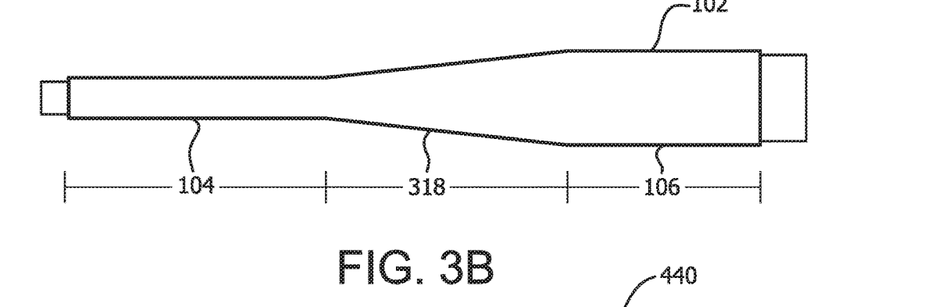
FIG. 3B is a side view of a tapered implantable device in a stage of formation.

FIGS. 3A and 3B illustrate an example step in a method to form a tapered implantable implant. Polymeric tubular member 102 is fitted over a first mandrel 330. First mandrel 330, as shown in FIG. 3A, comprises a smaller diameter length segment 334, a larger diameter length segment 336, and a first, longer tapered length segment 338. First, longer tapered length segment 338 is typically located between smaller diameter length segment 334 and larger diameter length segment 336.

In various embodiments, polymeric tubular element 102 initially comprises a diameter (consistent along its length) equal to or slightly less than the diameter of smaller diameter length segment 334. Polymeric tubular member 102 is placed around the exterior surface of first mandrel 330 and pulled onto the mandrel in the direction of the first larger diameter length segment 336. In various embodiments, as polymeric tubular member 102 is fitted over first mandrel 330 it is stretched over first, longer tapered length segment 338 to larger diameter length segment 336, forming second larger diameter length portion 106 and tapered portion having a first longer length 318.

In various embodiments, the respective lengths of larger diameter length portion 104 and smaller diameter length portion 106 can be selected to position tapered portion having a first longer length 318 at a desired position onto polymeric tubular member 102. For example, a tapered implantable device having a particular length of a larger diameter and particular length of a shorter diameter may be desired. It can also be appreciated that the tapered implantable device may be continuously tapered between the opposing ends of the device. By providing a method for placing a tapered portion having a multiplicity of bent fibrils between a smaller diameter length portion 104 and a larger diameter length portion 106, a tapered implantable device 100 having at least sufficient length of smaller diameter length portion 104 and larger diameter length portion 106 can be formed. In such embodiments, tapered implantable device 100 can be sized by, for example, cutting one or both ends of polymeric tubular member 102 such that a sufficient length of smaller diameter length portion 104 and larger diameter length portion 106 is provided.

Prior to removal of polymeric tubular member 102 from first mandrel 330, member 102 can be exposed to further processing steps. For example, polymeric tubular member 102 can be wrapped with a biocompatible reinforcing film, such as an ePTFE film. Any biocompatible material capable of reinforcing polymeric tubular member 102 is within the scope of the present disclosure.

For example, a length portion of polymeric tubular member 102, such as tapered length portion with a first longer length 318, can be heated. Further, heat can be applied to the entire first mandrel 330 and polymeric tubular member 102. Any processing of polymeric tubular member 102, including tapered length portion having a first longer length 318, is within the scope of the present disclosure.

In various embodiments, the outer surface of porous tubular member 102 can be coated with an elastomer. For example, as referenced in U.S. Pat. No. 8,029,563, a silicone composition such as MED-1137 Adhesive Silicone Type A from NuSil Silicone Technology (Carpenteria, Calif.) can be applied to the outer surface of porous tubular member 102. In various embodiments, the elastomer is applied after porous tubular member 102 is heated. Any application of elastomer to porous tubular member 102 is within the scope of the present disclosure.

Further, prior to removal from first mandrel 330, porous tubular member 102 can be surrounded by an optional second porous tubular member. In various embodiments, the optional second porous tubular member comprises a larger inner diameter than an outer diameter of the porous tubular member 102. The optional second porous tubular member can be positioned concentrically around first tubular member 102 on mandrel 330.

Figure 4A:
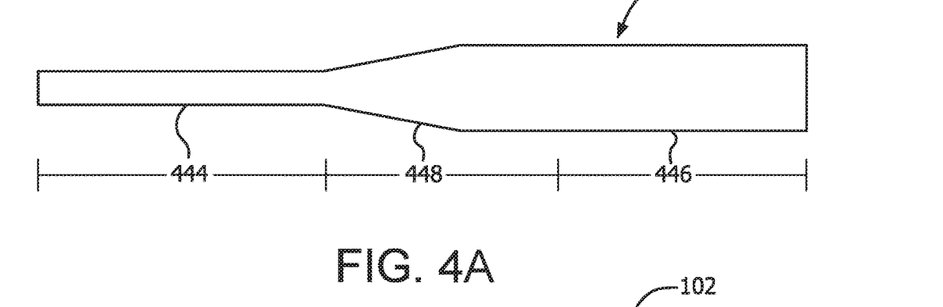
FIG. 4A is a side view of a second tapered mandrel.

As illustrated in FIG. 4A, a second mandrel 440 can comprise a larger diameter length segment 446, a smaller diameter length segment 444, and a second, shorter tapered length segment 448. Second, shorter tapered length segment 448 is typically located between smaller diameter length segment 444 and larger diameter length segment 446.

Figure 4B:
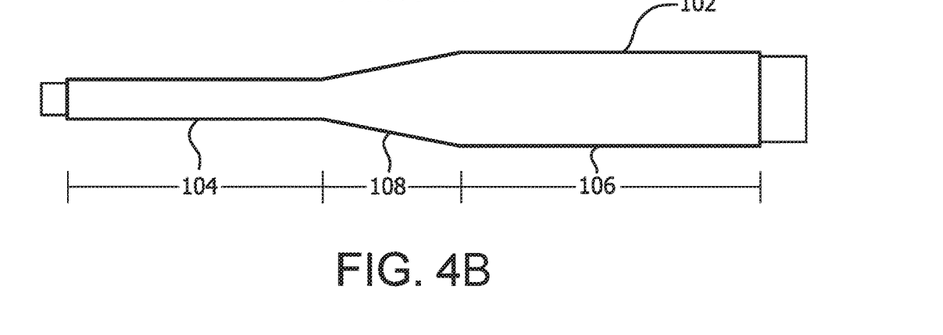
FIG. 4B is a side view of a tapered implantable device in another stage of formation.

With reference to FIG. 4B, polymeric tubular member 102 having a tapered portion with a first longer length 318 can be fitted over second tubular mandrel 440 such that tapered length portion 318 is located at or near second, shorter tapered length segment 448. Polymeric tubular member 102 can then be compressed longitudinally along second mandrel 440 in the direction of a larger diameter length segment 446, which converts tapered portion having a first longer length 318 to a tapered portion having a second shorter length 108. In such embodiments, shorter diameter length portion 104 and longer diameter length portion 106 of polymeric tubular member 102 do not experience a significant length change, as only tapered portion having a first longer length 318 is compressed against an exterior surface of second mandrel 440. As such, as previously described, the desired dimensions of tapered implantable device 100 can be selected prior to formation of tapered portion having a second shorter length 108.

A compression ratio can be used to describe the amount of longitudinal compression applied to tapered portion having a first longer length 318. For example, a compression ratio can comprise a ratio of the length tapered portion having a second shorter length 108 to the length of tapered portion having a first longer length 318. In various embodiments, the compression ratio can be between about 75% and 95%. In other embodiments, the compression ratio can be between about 50% and 75%. In yet other embodiments, the compression ratio can be between about 25% and 50%. The compression ratio may range as low as about 15%, and is largely dependent on the bulk density of the chosen porous precursor material.

In various embodiments, the compression ratio can correlate with the respective lengths of tapered portion having a second shorter length 108 and tapered portion having a first longer length 318. For example, a mandrel ratio can comprise the ratio of the length of second, shorter tapered length segment 448 to the length of first, longer tapered length segment 338. Preferably, the compression ratio and the mandrel ratio are substantially the same. In other embodiments, the mandrel ratio is within 10% of the compression ratio. In yet other embodiments, the mandrel ratio is within 33% of the compression ratio. Any correlation between the compression ratio and the mandrel ratio is within the scope of the present disclosure.

Figure 4C:
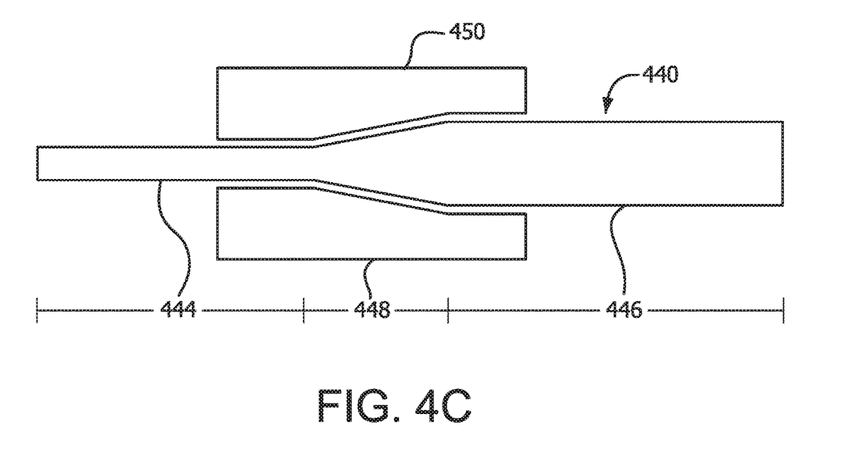
FIG. 4C is a side view of a second tapered mandrel and complimentary female die.

In various embodiments, as illustrated in FIG. 4C, a female die 450 can be used to assist in formation of tapered portion having a second shorter length 108. For example, female die 450 can apply a longitudinally compressive force against polymeric tubular member 102 at or near second, shorter tapered length segment 448, causing tapered portion having a first longer length 318 to compress against second, shorter tapered length segment 448 of second mandrel 440. Female die 450 can comprise, for example, a complementary shape to second, shorter tapered length segment 448 of second mandrel 440. In other embodiments, female die 450 comprises a shape different from that of second, shorter tapered length segment 448. In such embodiments, female die 450 can assist in providing a desired shape on an external surface of polymeric tubular member 102, including tapered portion having a second shorter length 108.

Further, female die 450 can assist in providing a consistent thickness of polymeric tubular member 102 in the smaller diameter region 104 and/or the tapered portion having a second shorter length 108. Any configuration of female die 450 that assists in forming tapered portion having a second shorter length 108 in a porous tubular member is within the scope of the present disclosure.

Prior to removal of polymeric tubular member 102 from second mandrel 440, member 102 can be exposed to further processing steps. For example, a portion of polymeric tubular member 102, such as tapered portion with a second shorter length 108, can be heated. Further, heat can be applied to the entire second mandrel 440 and polymeric tubular member 102. Any processing of polymeric tubular member 102, including tapered portion having a second shorter length 108, is within the scope of the present disclosure.

After formation of tapered portion having a second shorter length 108, tapered implantable device 100 can be removed from second mandrel 440 and prepared for use in the anatomy of a patient. In various embodiments, tapered implantable device 100 can be combined with a medical device such as, for example, a stent. In other embodiments, tapered implantable device 100 can be used without combination with another medical device. In such embodiments, tapered implantable device 100 can comprise a graft. Although described in particular embodiments, tapered implantable device 100 can be used alone or in combination with any suitable medical device for implantation within the anatomy of a patient.

Several characteristics and advantages have been set forth in the preceding description, including various alternatives together with details of the structure and function of the devices and methods. The disclosure is intended as illustrative only and as such is not intended to be exhaustive or limiting. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein.

What is claimed is:

1. An implantable article comprising:
   an expanded polytetrafluoroethylene (ePTFE) tube comprising a first length portion having a first diameter and a second length portion having a second diameter; and
   a tapered length portion between the first length portion and the second length portion and having a shorter length than at least one of the first length portion and the second length portion, wherein the tapered length portion comprises a multiplicity of compressed bent fibrils such that the tapered length portion is characterized by a tapered length portion rapid recovery property with a compression ratio between 30% and 95%, a difference between an extended length of the tapered length portion and a recovered length of the tapered length portion, that differs from a first rapid recovery property, a difference between an extended length of the first length portion and a recovered length of the first length portion, characterizing the first length portion.

2. The implantable article of claim 1, wherein the tapered length portion comprises a uniform, frustoconical shape.

3. The implantable article of claim 1, wherein the compression ratio of the tapered length portion is between 50% and 95%.

4. An implantable article comprising:
   an expanded polytetrafluoroethylene (ePTFE) tube comprising a first length portion having a smaller diameter and a second end having a larger diameter; and
   a tapered length portion between the first length portion and the second end and having a shorter length than at least one of the first length portion and the second length portion, wherein the tapered length portion comprises a multiplicity of compressed bent fibrils such that the tapered length portion is characterized by a rapid recovery property with a compression ratio between 30% and 95%, a difference between an extended length of the tapered length portion and a recovered length of the tapered length portion, that is greater than a rapid recovery property of the first length portion.

5. The implantable article of claim 4, wherein the compression ratio of the tapered length portion is between 50% and 95%.

6. An implantable article comprising:
   an ePTFE tube comprising a first length portion having a first diameter and a second length portion having a second diameter; and
   a tapered length portion that includes a uniform frustoconical section between the first length portion and the second length portion and having a shorter length than at least one of the first length portion and the second length portion, wherein the tapered length portion comprises a multiplicity of compressed bent fibrils characterized by a tapered length portion rapid recovery property with a compression ratio between 30% and about 95%, a difference between an extended length of the tapered length portion and a recovered length of the tapered length portion, that differs from a rapid recovery property, a difference between an extended length of the first length portion and a recovered length of the first length portion, characterizing the first length portion.

7. The implantable article of claim 6, wherein the ePTFE tube comprises a multiplicity of bent fibrils.

8. The implantable article of claim 6, wherein the tapered length portion comprises a non-uniform shape.

9. The implantable article of claim 6, wherein the tapered length portion comprises a uniform, frustoconical shape.

10. The implantable article of claim 6, wherein the tapered length portion is characterized by a tapered length portion rapid recovery property that is greater than a rapid recovery property characterizing the first length portion.

11. The implantable article of claim 6, wherein the compression ratio of the tapered length portion is between 50% and 95%.

12. An implantable article comprising:
    an ePTFE tube comprising a first end having a smaller diameter and a second end having a larger diameter; and
    a tapered length portion between the first end and the second end and having a shorter length than at least one of the first length portion and the second length portion, wherein the tapered length portion comprises a multiplicity of compressed bent fibrils characterized by a tapered length portion rapid recovery property with a compression ratio between 25% and 95%, a spring like-property that comprises a difference between an extended length of the tapered length portion and a recovered length of the tapered length portion, that differs from a rapid recovery property, a difference between an extended length of the first length portion and a recovered length of the first length portion, characterizing the first length portion.

13. The implantable article of claim 12, wherein the ePTFE tube further comprises a first length portion having the smaller diameter and a second length portion having the larger diameter.

14. The implantable article of claim 12, wherein the ePTFE tube comprises a multiplicity of bent fibrils.

15. The implantable article of claim 12, wherein the tapered length portion comprises a non-uniform shape.

16. The implantable article of claim 12, wherein the tapered length portion comprises a uniform, frustoconical shape.

17. The implantable article of claim 12, wherein the tapered length portion is characterized by a greater rapid recovery property than the first length portion.

18. The implantable article of claim 12, wherein the tapered length portion is characterized by a tapered length portion rapid recovery property that is greater than a rapid recovery property characterizing the first length portion.

19. The implantable article of claim 12, wherein the compression ratio of the tapered length portion is between 50% and 95%.

* * * * *